United States Patent [19]

Moura et al.

[11] Patent Number: 5,130,329
[45] Date of Patent: Jul. 14, 1992

[54] BENZOCYCLOHEXANES AND BENZOCYCLOHEPTANES USEFUL AS ANALGESICS

[75] Inventors: Anne-Marie Moura; François Clemence; Daniel Frechet; Michel Fortin, all of Paris, France

[73] Assignee: Roussel Uclaf, Paris, France

[21] Appl. No.: 591,283

[22] Filed: Oct. 1, 1990

Related U.S. Application Data

[63] Continuation-in-part of Ser. No. 312,885, Feb. 17, 1989, Pat. No. 5,068,244.

[30] Foreign Application Priority Data

Feb. 18, 1988 [FR] France .................. 88 01928

[51] Int. Cl.$^5$ .................. A61K 31/40; C07D 207/06
[52] U.S. Cl. .................. 514/429; 514/237.8; 514/255; 514/319; 514/428; 544/166; 544/393; 546/205; 548/568
[58] Field of Search .................. 514/429, 428, 237.8, 514/255, 319, 617, 619; 544/166, 393; 546/205; 548/568; 564/166, 182

[56] References Cited

U.S. PATENT DOCUMENTS 4,876,269 10/1989 Penner et al. .................. 514/429

FOREIGN PATENT DOCUMENTS 0260555 3/1988 European Pat. Off. .

Primary Examiner—Joseph Paul Brust
Assistant Examiner—Jacqueline Haley
Attorney, Agent, or Firm—Bierman and Muserlian

[57] ABSTRACT

Novel all possible enantiomeric and diastereoisomeric forms of compounds of the formula

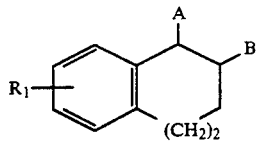

wherein $R_1$ is selected from the group consisting of hydrogen, halogen, alkyl and alkoxy of 1 to 5 carbon atoms, $-NO_2$, $-NH_2$ and mono and dialkylamino of 1 to 5 alkyl carbon atoms, A and B have the trans configuration, one of A and B being

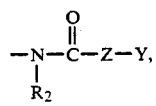

$R_2$ is hydrogen or alkyl of 1 to 5 carbon atoms, Z is $-(CH_2)_{n2}$, $n_2$ being an integer from 0 to 5 or branched alkylene of 2 to 8 carbon atoms or $-CH_2-O-$, Y is selected from the group consisting of phenyl, naphthyl, indenyl, heteromonocycle of 5 to 6 ring atoms and heterobicycle, all optionally having at least one substituent and the other of A and B is

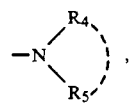

$R_4$ and $R_5$ individually being selected from the group consisting of hydrogen and alkyl of 1 to 5 carbon atoms or taken together with the nitrogen to which they are attached form a 5 to 6 ring heterocycle optionally containing a heteroatom selected from the group consisting of $-O-$, $-S-$ and $-NH-$ and their non-toxic, pharmaceutically acceptable acid addition salts having central analgesic properties and a strong affinity for opiate receptors.

18 Claims, No Drawings

BENZOCYCLOHEXANES AND BENZOCYCLOHEPTANES USEFUL AS ANALGESICS

PRIOR APPLICATION

This application is a continuation-in-part of U.S. Pat. application Ser. No. 312,885 filed Feb. 17, 1989, now U.S. Pat. No. 5,068,244.

STATE OF THE ART

Related compounds are described in French patent NO. 2,370,273 and European patent applications No. 129,991, No. 147,085 and No. 260,555.

OBJECTS OF THE INVENTION

It is an object of the invention to provide the novel compounds of formula I and their non-toxic, pharmaceutically acceptable acid addition salts and a process and novel intermediates for their preparation.

It is another object of the invention to provide analgesic compositions and a novel method of relieving pain in warm-blooded animals.

These and other objects and advantages of the invention will become obvious from the following detailed description.

THE INVENTION

The novel compounds of the invention are selected from the group consisting of all possible enantiomeric and diastereoisomeric forms of compounds of the formula

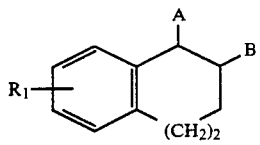

wherein $R_1$ is selected from the group consisting of hydrogen, halogen, alkyl and alkoxy of 1 to 5 carbon atoms, $-NO_2$, $-NH_2$ and mono and dialkylamino of 1 to 5 alkyl carbon atoms, A and B have the trans configuration, one of A and B being

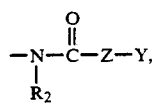

$R_2$ is hydrogen or alkyl of 1 to 5 carbon atoms, Z is $(CH_2)-_{n2}$, $n_2$ being an integer from 0 to 5 or branched alkylene of 2 to 8 carbon atoms or $-CH_2-O-$, Y is selected from the group consisting of phenyl, naphthyl, indenyl, heteromonocycle of 5 to 6 ring atoms and heterobicycle, all optionally having at least one substituent and the other of A and B is

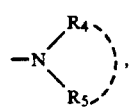

, $R_4$ and $R_5$ individually being selected from the group consisting of hydrogen and alkyl of 1 to 5 carbon atoms or taken together with the nitrogen to which they are attached form a 5 to 6 ring heterocycle optionally containing a heteroatom selected from the group consisting of $-O-$, $-S-$ and $-NH-$ and their non-toxic, pharmaceutically acceptable acid addition salts.

When Y is phenyl substituted with at least one substituent, the substituents are at least one member of the group consisting of alkyl and alkoxy of 1 to 5 carbon atoms, halogens, $-CF_3$, $-NO_2$, $-NH_2$ and mono- and dialkylamino.

Examples of $R_1$ and Y substituents on the phenyl are alkyl such as n-butyl, isobutyl, n-pentyl and preferably methyl, ethyl, n-propyl or isopropyl, alkoxy such as n-propoxy, isopropoxy, n-butoxy, sec-butoxy, tert.-butoxy and preferably methoxy or ethoxy and halogen such as fluorine, bromine and iodine and preferably chlorine.

Examples of mono- and dialkylamine are those wherein the alkyl is methyl or ethyl.

Examples of Y as a heteromonocycle of 5 to 6 ring atoms are thiazolyl, pyridinyl, oxazolyl, isoxazolyl, imidazolyl and thienyl and as a heterobicycle are indoyl, quinolyl, benzofuranyl, benzo[b]thienyl, benzimidazolyl, benzoxazolyl and benzothiazolyl. When Y is substituted naphthyl, indentyl, heteromonocycle or heterobicycle, the substituents are preferably one or two members of the group consisting of methyl, ethyl, methoxy, ethoxy chlorine, bromine, fluorine, $-CF_3$, $-NO_2$ or phenyl.

When Z is $(CH_2)_{n2}-$, $n_2$ is preferably 0 or 1 and when Z is branched alkylene, it is preferably substituted with 1 or more methyls or ethyls such as 1,1-ethanediyl, methyl-1-ethanediyl-1,2, methyl-1 or 2-propanediyl-1,2- and ethyl-1-ethanediyl-1,2. Examples of $R_4$ and $R_5$ taken together with the nitrogen atom are pyrrolidinyl, piperazinyl, piperidinyl and morpholinyl.

Examples of suitable acids for the preparation of the nontoxic, pharmaceutically acceptable acid addition salts are hydrochloric acid, hydrobromic acid, nitric acid, sulfuric acid, phosphoric acid, acetic acid, propionic acid, formic acid, benzoic acid, maleic acid, fumaric acid, succinic acid, tartaric acid, citric acid, oxalic acid, glyoxylic acid, aspartic acid, alkanesulfonic acids such as methanesulfonic acid, and arylsulfonic acids such as benzenesulfonic acid.

Among the preferred compounds of formula I are those wherein in the group

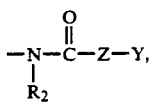

$R_2$ is methyl or ethyl, Z is $-(CH_2)_n-$, $n_2$ is 0 or 1 or

or $-CH_2O-$ and Y is pyrrolidinyl, those wherein in the group

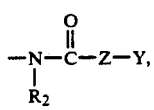

Y is selected from the group consisting of naphthyl, benzo[b]thiophene or phenyl optionally substituted with at least one member of the group consisting of methyl, ethyl, methoxy, ethoxy, chlorine, bromine, —CF₃ and —NO₂, and those wherein R₁ is hydrogen, A is

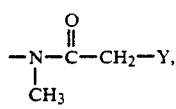

Y is 3,4-dimethoxy-phenyl, 3,4-dichloro-phenyl, 4-trifluoromethylphenyl, 4-nitro-phenyl or benzothienyl and B is pyrrolidinyl and their non-toxic, pharmaceutically acceptable acid addition salts.

Specific preferred compounds of formula I are trans (±) 4-nitro-N-methyl-N-[(2-(1-pyrrolidinyl)-1,2,3,4-tetrahydro-1-naphthyl]-benzene-acetamide; trans (±) N-methyl-N-[2-(1-pyrrolidinyl)-1,2,3,4-tetrahydro-1-naphthyl]-1-naphthalene-acetamide; and trans (±) N-methyl-N-[2-(1-pyrrolidinyl)-1,2,3,4-tetrahydro-1-naphthyl]-4-benzo-[b]-thiophene-acetamide and their non-toxic, pharmaceutically acceptable acid addition salts.

The novel process of the invention for the formation of compounds of formula I comprises reacting a compound of the formula

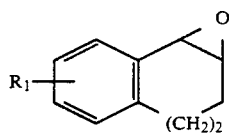 II wherein R₁ has having the above meaning with either an amine of the formula

 III wherein R₂ has the above definition and R₃ is a protective group of the amine function to obtain a product of the formula

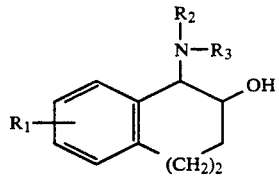 IV wherein the hydroxyl function is activated and is condensed with an amine of the formula

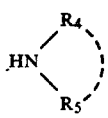

wherein R₄ and R₅ have the above definition to obtain a compound of the formula

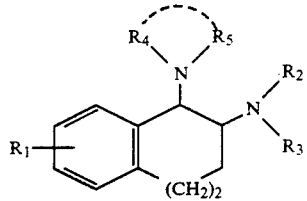 V eliminating the protective group of the amine function to obtain a product of the formula

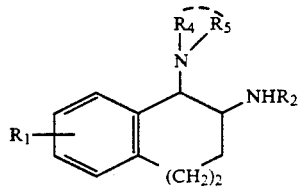 VI reacting the latter with an acid or a functional derivative of an acid of the formula

Y—Z—COOH     VII wherein Y and Z have the above definition to obtain a product of formula I in which A is

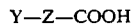

and B is

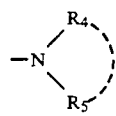

or with an amine of the formula

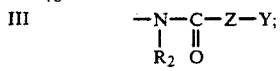

to obtain a product of the formula

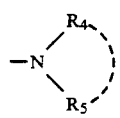 VIII activating the hydroxyl function and reacting the latter with an amine of the formula

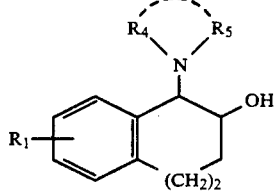     IX

in which $R_2$ has the above definition to obtain a product of the formula

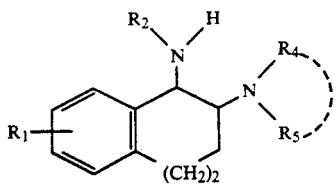

reacting the latter with an acid or a functional derivative of an acid of the formula $$Y-Z-COOH \qquad \text{VII}$$

in which Z and Y have the above definition to obtain a product of formula I in which A is

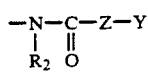

and B is

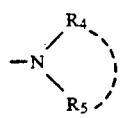

the said compounds of formula I being abe to be resolved to obtain the optically active forms, and treated, if desired, with mineral or organic acid to obtain the salts.

In a preferred mode of the process of the invention, methanesulfonyl chloride is used to activate the hydroxyl function of the products of formulae IV and VIII and in the products of formula V, the protective group $R_3$ is benzyl which can be eliminated by catalytic hydrogenation. The catalyst used is preferably palladium. The condensation of the compound of formula VII with the compound of formula VI or X is carried out in the presence of carbonyldiimidazole. A functional derivative of the acid of formula VII such as an acid chloride or a mixed anhydride can equally be used. The products of formula I can be resolved by the usual methods.

The novel analgesic compositions of the invention are comprised of an analgesically effective amount of at least one compound of formula I and their non-toxic, pharmaceutically acceptable acid addition salts and an inert pharmaceutical carrier or excipient. The compositions may be in the form of tablets, dragees, gelules, granules, suppositories, ointments, creams gels, injectable solutions or aerosols.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting agents, dispersants and emulsifiers and preservatives.

The compositions are useful for alleviation of pain irrespective of its origin, for example pain of a muscular, articulatory or nervous nature. They can also be used in the treatment of toothaches, migraines, shingles, in the treatment of intense pain, particularly resistant to peripheral antalgics, for example in the course of neoplasic process, in the treatment of pancreatic, nephrocolic or biliary colic, in the treatment of post-operation and post-trauma pain.

Besides of their analgesic activity, the compositions have a strong affinity for opiate receptors, particularly Kappa receptors and possess diuretic properties, anti-arhythmic, anti-ischemic cerebral and hypotensive properties. They are therefore useful for the treatment of arhythmia and the treatment of oedematous syndromes, cardiac deficiencies, certain obesity, cirrhosis, in the treatment of severe and refractory oedema, particularly those of congestive deficiency and in the long-term treatment of arterial hypertension.

The novel method of the invention for relieving pain in warm-blooded animals, including humans, comprises administering to warm-blooded animals an analgesically effective amount of at least one compound of formula I and their non-toxic, pharmaceuticaly acceptable acid addition salts. The compounds may be administered orally, rectally, parenterally or topically and the daily dose is 0.066 to 13.33 mg/kg depending on the compound used, the method of administration and the condition treated. For example, the daily parenteral dose is 0.066 to 1.33 mg/kg while the oral dose is 0.266 to 5.33 mg/kg.

The novel intermediates of the invention are the compounds of formulae IV, V, VI, VIII and X.

The compounds of formula II wherein $R_1$ is hydrogen are described in J. Org. Chem., Vol. 44, No. 8, (1979), p. 1342.

When $R_1$ is other than hydrogen, the starting epoxide of formula II may be prepared by reacting a brominated derivative with an alkali metal hydroxide or sodium hydride according to the following reaction scheme:

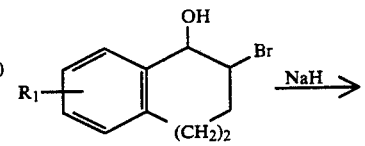

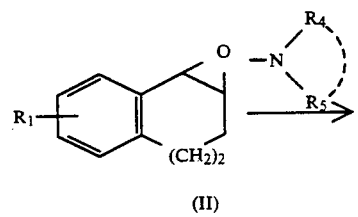

(II)

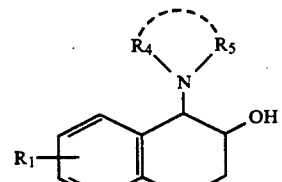

(VIII)

In the following examples there are described several preferred embodiments to illustrate the invention. However, it should be understood that the invention is not intended to be limited to the specific embodiments.

EXAMPLE 1

(E) butenedioate of (± trans)
3,4-dimethoxy-N-methyl-N-[2-(1-pyrrolidinyl)-1,2,3,4-tetrahydro-1-naphthyl]-benzene acetamide

STEP A: trans (3S)-1-(1-pyrrolidinyl)-1,2,3,4-tetrahydro-2-naphthol

A solution of 8.8 g of 1a2,3,7b-tetrahydro-naphtho[1,2-b]oxirene [J. Am. Chem. Soc., Vol. 101 (19), 5679–87 (1979)], 18 ml of water and 18 ml of pyrrolidine was heated to 70° C. for 30 minutes, then concentrated under reduced pressure in a bath at 50° C., extracted with ether, washed with water, dried, filtered and concentrated to dryness under reduced pressure in a bath at 50° C. to obtain 10.8 g of brown oil containing the expected product.

STEP B: Trans (3S) N-methyl-2-(1-pyrrolidinyl)-1,2,3,4-tetrahydro-1-naphthalene amine A solution of 10.8 g of the product of Step A, 100 ml of tetrahydrofuran and 9.7 ml of triethylamine was cooled to −20° C. and then over 10 minutes, 5.5 ml of methanesulfonyl chloride were added. The precipitate was allowed to return to ambient temperature and then 38 ml of methylamine at 33% in ethanol were added. The mixture was stirred for 20 hours and the tetrahydrofuran and the ethanol were eliminated under reduced pressure at 50° C. 100 ml of water and 10 ml of a solution of sodium hydroxide were added and extraction was done with methylene chloride. The extracts were washed with water, dried, filtered and concentrated to dryness to obtain 11.5 g of the expected product as a brown oil.

STEP C: (E) butenedioate of (± trans) 3,4-dimethoxy-N-methyl-N-[2-(1-pyrrolidinyl)-1,2,3,4-tetrahydro-1-naphthyl]-benzene-acetamide 3 g of carbonyl-diimidazole were added all at once to a solution of 4.1 g of 3,4-dimethoxyphenyl acetic acid in 26 ml of tetrahydrofuran. The mixture was stirred for 1 hour at ambient temperature, and 3 g of the product of Step B in 27 ml of tetrahydrofuran were added quickly. The mixture was stirred for 2 hours at ambient temperature and the tetrahydrofuran was eliminated under reduced pressure in a bath at 50° C. The residue was dissolved in a saturated solution of sodium bicarbonate and the solution was extracted with methylene chloride. The organic phase was washed with water, dried, filtered, and concentrated by dryness under reduced pressure at 50° C. to obtain 5.5 g of the expected product in the form of a base which was dissolved in 60 ml of isopropanol. A solution of 1.51 g of fumaric acid in 40 ml of methanol was added and the mixture was concentrated to 70 ml. Crystallization was induced and the mixture stood for 1 hour at ambient temperature. The crystals were separated, washed with isopropanol and dried under reduced pressure at 90° C. to obtain 4.44 g of crude product in the form of a salt which was purified by two successive crystallizations from ethanol to obtain 3.13 g of the expected product in the form of a fumarate salt melting at 200° C.

Analysis: Calculated: %C 66.39, % H 6.92, %N 5.34, Found: 66.5, 6.9, 5.3.

EXAMPLE 2

Trans (±) N-methyl-4-nitro-N-[2(1-pyrrolidinyl)-1,2,3,4-tetrahydro-1-naphthyl]-benzene acetamide Using the procedure of Step C of Example 1, 770 mg of (p-nitrophenyl) acetic acid and 700 mg of the product of Step B of Example 1 were reacted to obtain 1.4 g of crude product which was purified by chromatograph on silica (eluant: methylene chloride 90, methanol 10) to obtain 1.1 g of product which was crystallized from ethyl ether to obtain 480 mg of product. Two crystallizations from isopropanol were effected to obtain 300 mg of the expected product melting at 135° C.

Analysis: Calculated: %C 70.21, %H 6.92, %N 10.68; Found: 70.3, 7.0, 10.6.

EXAMPLE 3

Trans (±) N-methyl-N-[2-(1-pyrrolidinyl)-1,2,3,4-tetrahydro-1-naphthyl]-1-naphthalene acetamide Using the procedure of Step C of Example 1, 2.3 g of 1-naphthylacetic acid and 2 g of the product of Step B of Example 1 were reacted to obtain 5.3 g of crude product which was purified by chromatography on silica (methylene chloride 9-methanol 1). After crystallization from ethyl ether, 1.9 g of product melting at 117° C. were obtained which was crystallized from isopropyl ether to obtain 1.1 g of the expected product melting at 125° C.

Analysis: Calculated: %C 81.37, %H 7.59, %N 7.03; Found: 81.7, 7.6, 7.0.

EXAMPLE 4

Trans (±) 3,4-dichloro-N-methyl-N-[2-(1-pyrrolidinyl)-1,2,3,4-tetrahydro-1-naphthyl]-benzamide 478 mg of the product of Step B in Example 1 were dissolved at ambient temperature in 15 ml of anhydrous ethyl ether and 870 mg of 3,4-dichloro-benzoyl chloride were added in 4 lots. The mixture was stirred for 1 hour, separated and washed with ethyl ether to obtain 520 mg of the expected product in the form of its hydrochloride. The formation of the free base was effected by adding 40 ml of water, then 10 ml of 2N sodium hydroxide. The mixture was extracted with methylene chloride. The organic phase was washed with 2N sodium hydroxide, dried and concentrated to dryness under reduced pressure to obtain 500 mg of product which was dissolved in 5 ml of ethyl acetate. The mixture was filtered, concentrated and 2.5 ml of isopropyl ether were added. Then crystallization was induced and the mixture stood for 1 hour at ambient temperature and the crystals were separated to obtain 215 mg of the expected product melting at 138° C.

Analysis: Calculated: %C 65.51, %H 6.0, %Cl 17.58, %N 6.94; Found: 65.5, 5.9, 17.9, 6.9.

EXAMPLES 5 AND 6

Hydrochloride of [(5α,6β)(±)]3,4-dichloro-N-α-dimethyl-N-[6-(1-pyrrolidinyl)-6,7,8,9-tetrahydro-5H-benzocyclohepten-5-yl]-benzene acetamide Example 5: Diastereo isomer A
Example 6: Diastereo isomer B

STEP A: Trans (±) 5-(1-pyrrolidinyl)-6,7,8,9-tetrahydro-5H-benzocyclohepten-6-ol 6 g of a 1a,3,4,8b-tetrahydro-2H-benzo[3,4]-cyclohept [1,2,b]oxirene [J. Org. Chem., Vol. 44, No. 8, 1979, 1342] were added to 12 ml of water and 12 ml of pyrrolidine were added with stirring for 20 minutes on a bath at 70° C. After concentrating to dryness under reduced pressure, dissolving in 200 ml of ethyl ether, drying, treating with active carbon, filtering, and concentrating to dryness under reduced pressure, 8.2 g of orange-colored oil were obtained.

STEP B: Trans (±) N-methyl-6-(1-pyrrolidinyl)-6,7,8,9-tetrahydro-5H-benzoycyclohepten-5-amine 8.2 g of the product of Step A were dissolved in 82 ml of tetrahydrofuran and 7 ml of triethylamine and after the mixture was cooled in a bath to −20° C., 3.9 ml of methane sulfonyl chloride in solution in 8 ml of tetrahydrofuran were added. After returning to ambient temperature, 35 ml of methylamine at 33% in ethanol were added and the mixture was stirred for 23 hours. The solvents were eliminated under reduced pressure and 150 ml of water and 10 ml of a solution of sodium hydroxide were added. Extraction was effected with methylene chloride and the extracts were washed with salted water, dried, filtered and concentrated to dryness under reduced pressure to obtain 8.7 g of the expected products as an orange-colored oil.

STEP C: Hydrochloride of [(5α,6β) (±)3,4-dichloro-N-α-dimethyl-N-[6-(1-pyrrolidinyl)-6,7,8,9-tetrahydro-5H-benzocyclohepten-5-yl]-benzene acetamide 1.6 g of 3,4-dichloro-α-methyl-benzene acetic acid and 1.2 g of 1,1′-carbonyldiimidazole were dissolved in 16 ml of tetrahydrofuran and the mixture was stirred for 30 minutes. Then a solution of 1 g of the product of Step B in 16 ml of tetrahydrofuran was added all at once and the mixture was stirred under a current of nitrogen while the solution was refluxed for 12 hours and 30 minutes. The tetrahydrofuran was eliminated under reduced pressure and 50 ml of saturated sodium bicarbonate solution and 30 ml of water were added. Extraction was effected with methylene chloride and the extracts were washed with a saturated solution of sodium chloride, dried and concentrated under reduced pressure to obtain 2.45 g of crude product. The latter was purified by chromatograph on silica (eluant : methylene chloride 90-methanol 10) to obtain 580 mg of product having an Rf of 0.6 corresponding to the diastereo isomer A in the form of abase (Example 5) and 920 mg of product having an Rf of 0.35 corresponding to the diastereo isomer B in the form of a base (Example 6).

Diastereo isomer A was dissolved in 10 ml of ethyl acetate and 2 ml of a hydrochloride acid—ethyl acetate solution was added. The mixture stood for 48 hours and was filtered and washed with ethyl ether to obtain 730 mg of product which was dissolved in 20 ml of methylene chloride, treated with active charcoal, filtered and concentrated. 30 ml of ethyl ether were added and the mixture stood for crystallization for 16 hours. The crystals were separated and washed with ethyl ether to obtain 578 mg of the expected product. The latter was dissolved in 100 ml of isopropanol, concentrated, stood for 18 hours, dried, washed with isopropanol and with ethyl ether and dried under reduced pressure at 80° C. to obtain 458 mg of the expected product melting at 230° C. then 252° C.

Analysis: Calculated: %C, 62.31, %H 6.48, %N 5.81, %Cl 22.07; Found: 62.2, 6.5, 5.6, 22.0.

The hydrochloric of diastereo isomer B was obtained in a similar way as the hydrochloride of diastereo isomer A to obtain 785 mg of the product in the form of a hydrochloride melting at 240° C.

Analysis: Calculated %C 62.31 %H 6.48, %N 5.81, %Cl 22.07; Found: 62.4, 6.5, 5.8, 21.9.

EXAMPLE 7

(E) butenedioate of (± trans) 3,4-dimethoxy-N-methyl-N-[6-(1-pyrrolidinyl)-6,7,8,9-tetrahydro-5H-benzocyclo-hepten-6-yl]-benzene acetamide Using the procedure of Step C of Examples 5 and 6, 3.92 g of 3,4-dimethoxy-phenylacetic acid and 3 g of the product of Step B of the Examples 5 and 6 were reacted to obtain 5 g of the product in the form of a base. 75 ml of isopropanol and 1.37 g of fumaric acid in 20 ml of methanol were added and crystallization was induced. After standing overnight, the crystals were separated, washed with isopropanol and dried at 100° C. under reduced pressure to obtain 4.3 g of the expected product in the form of a fumarate salt melting at 190° C.

Analysis: Calculated: %C 66.89, %H 7.12, %N 5.20, Found: 66.6, 7.0, 5.1.

EXAMPLE 8

(E) 2-butenedioate of trans (±) 3,4-dichloro-N-methyl-N-[6-(1-pyrrolidinyl)-6,7,8,9-tetrahydro-5H-benzocyclo-hepten-5-yl]-benzene acetamide Using the procedure of Step C of Examples 5 and 6, 10.5 g of 3,4-dichlorophenyl acetic acid and 8.7 g of the product of Step B of Examples 5 and 6 were reacted to obtain 16.7 g of the expected product in the form of a base. 150 ml of methanol were added and after treating with active charcoal and filtering, 4.18 g of fumaric acid in 100 ml of methanol were added. Crystallization was induced and after standing overnight, the crystals were separated, washed and dried under reduced pressure at 90° C. to obtain 15.1 g of the expected product in the form of a fumarate salt melting at 170° C., then 210° C.

Analysis Calculated: %C 61.43, %H 5.80, %Cl 12.95, %N 5.12; Found: 61.7, 5.9, 13.2, 5.3.

EXAMPLE 9

Trans (±) N-methyl-N-[6-(1-pyrrolidinyl)-6,7,8,9-tetrahydro-5H-benzocyclohepten-5-yl]-1-naphthalene acetamide Using the procedure of Step C of Examples 5 and 6, 630 mg of 1-naphthylacetic acid and 500 mg of the product of Step B of Examples 5 and 6 were reacted to obtain 1 g of yellow oil which was purified by chromatograph on silica (eluant : methylene chloride 90-methanol 10). After crystallization from ethyl ether, 613 mg of the expected product melting at 174° C. were obtained.

Analysis: Calculated %C 81.51, %H, 7.82, %N 6.79; Found: 81.2, 7.9, 6.7.

EXAMPLE 10

Hydrochloride of trans (±) 3,4-dichloro-N-methyl-N-[6-(1-pyrrolidinyl)-6,7,8,9-tetrahydro-5H-benzocyclohepten-5-yl]-benzamide 244 mg of the product of Step B of Examples 5 and 6 were dissolved in 8 ml of anhydrous ethyl ether and in four lots, 420 mg of freshly prepared 3,4-dichloro-benzoyl chloride were added followed by stirring for half an hour. After separating, washing with ethyl ether, and drying under reduced pressure of 40° C., 408 mg of crude product were obtained in the form of its hydrochloride.

The latter was dissolved in 2.5 ml of methylene chloride and 15 ml of ethyl ether were added. After standing for 16 hours, the product was evaporated and dried under reduced pressure at 80° C. to obtain 276 mg of product which was crystallized from 25 ml of methyl ethyl ketone and 15 ml of ethyl ether. The mixture stood for 4 hours, then was filtered and dried under reduced pressure to obtain 185 mg of the expected product in the form of hydrochloride melting at 240° C.

Analysis: Calculated: %C, 60.87, %H 6.0 %N .6.17, %Cl 23.43; Found: 60.8, 6.1, 6.2, 23.5.

EXAMPLE 11

Hydrochloride of trans (±) N-methyl-N-[6-(1-pyrrolidinyl)-6,7,8,9-tetrahydro-5H-benzocyclohepten-5-yl]-4-(trifluoromethyl)-benzene acetamide Using the procedure of Step C of Examples 5 and 6, 580 mg of p-trifluoromethylphenyl acetic acid and 492 mg of the product of Step B of Examples 5 and 6 were reacted to obtain 1.09 g of crude product which was purified by chromatography on silica (methylene chloride 9-methanol 1) to obtain 750 mg of the expected product in the form of a base. The latter was dissolved in 3 ml of ethyl acetate and 2 ml of a solution of hydrochloride acid—ethyl acetate (3.5N) and 1.5 ml of ethyl ether was added. Crystallization was induced and after standing for 48 hours, the crystals were separated, washed and dried under reduced pressure at 80° C. to obtain 659 mg of the product which was crystallized twice from ethyl ether to obtain 405 mg of the expected product in the form of its hydrochloride melting at 197° C.

Analysis: Calculated: %C 64.3 %H 6.47, %F 12.2, %N 6.0, %Cl 7.59; Found: 64.5, 6.5, 12.4, 5.9, 8.0-7.9.

EXAMPLE 12

Hydrochloride of trans (±) N-methyl-N-[6-(1-pyrrolidinyl)-6,7,8-9-tetrahydro-5H-benzoycyclohepten-5-yl]-4-nitro-benzene acetamide Using the procedure of Step C of Examples 5 and 6, 520 mg of p-nitrophenyl acetic acid and 497 mg of the product of Step B of Examples 5 and 6 were reacted to obtain 1.08 g of orange-colored oil which was purified by chromatography on silica (eluant : methylene chloride 90 methanol 100) to obtain 930 mg of the expected product in the form of a base which was converted into a hydrochloride as in Example 1 to obtain 765 mg of the expected hydrochloride product melting at 260° C.

Analysis: Calculated: %C 64.93, %H 6.81, %N 9.46, %Cl 7.98; Found: 64.9, 6.9, 9.5, 8.0.

EXAMPLE 13

(5α,6β) (±) N-methyl-N-[6-(1-pyrrolidinyl)-6,7,8,9-tetrahydro-5H-benzocyclohepten-5-yl]-benzo[b]thiophene-4-acetamide Using the procedure of Step C of Examples 5 and 6, 550 mg of 4-thionaphthene acetic acid and 500 mg of the product of Step B of Examples 5 and 6 were reacted to obtain 1.13 g of crude product which was purified by chromatography on silica (eluant : methylene chloride 90 methanol 10) to obtain 750 mg of product which was crystallized from ethyl ether to obtain 613 mg of product which was crystallized from methanol to obtain 400 mg of the expected product melting at 172° C.

Analysis Calculated: %C 74.6, %H 7.22, %N 6.69, %S 7.66; Found: 74.6, 7.3, 6.7, 7.7.

EXAMPLE 14

(E) 2-butenedioate of (± trans) 3,4-dimethoxy-N-methyl-N-[5-(1-pyrrolidinyl)-6,7,8,9-tetrahydro-5H-benzocyclohepten-6-yl]-benzene acetamide

STEP A: Trans (±) 5-[methyl-benzyl-amino]-6,7,8,9-tetrahydro-5H-benzocyclohepten-6-ol A solution of 6.8 g of 1a,3,4,8b-tetrahydro-2H-benzo[3,4]cyclohept[1,2,b]oxirene in 13.6 ml of water and 13.6 ml of benzylmethylamine was heated for 90 minutes at 100° C. and was then concentrated until nearly dry under reduced pressure. The residue was extracted with methylene chloride and the organic phase was washed with water, dried, filtered and concentrated to dryness under reduced pressure at 50° C. to obtain 13 g of a brown oil which was purified by chromatograph on silica with methylene chloride/ether 9/1 to obtain 11 g of oil which was crystallized from isopropyl ether at −4° C. The crystals were separated, washed with isopropyl ether and dried under reduced pressure at 40° C. to obtain 4.8 g of the expected product melting at 70° C.

3.6 of the product were chromatographed on silica (eluant : methylene chloride 9 ether 1) from the mother liquors and was crystallized at +4° C. from isopropyl ether. After separating, 2 g of the expected product melting at 70° C. were obtained.

STEP B: Trans (±) N-methyl-N-benzyl-5(1-pyrrolidinyl)-6,7,8,9-tetrahydro-5H-benzocyclohepten-6-amine A solution of 4.2 g of the product of Step A is 42 ml of anhydrous tetrahydrofuran and 2.9 ml of triethylamine was cooled to −20° C. and 1.63 ml of methane sulfonyl chloride in 3.25 ml of tetrahydrofuran were added. The temperature was brought back to the ambient and 7.5 ml of pyrrolidine were added. The mixture was stirred for 24 hours, and then concentrated under reduced pressure at 50° C. 90 ml of water and 10 ml of sodium hydroxide solution were added and the mixture was extracted with methylene chloride. The extracts were washed with water, dried, filtered and concentrated to dryness under reduced pressure to obtain 6.38 g of yellow oil. After chromatography (eluant : methylene chloride 95 methanol 5), 5 g of the product were obtained having a Rf of 0.3.

STEP C: Trans (±) N-methyl-5-(1-pyrrolidinyl) 6,7,8,9-tetrahydro-5H-benzocyclohepten-6-amine A solution of 2 g of the product of Step B in 40 ml of methanol and 2.6 ml of 22 Be hydrochloride acid was hydrogenated with 1.25 g of palladium under 1800 mmbars for 45 minutes. The mixture was filtered, rinsed with methanol and concentrated under reduced pressure at 50° C. The residue was dissolved in 10 ml of water which was alkalized with 2.6 ml of sodium hydroxide solution, and extracted with methylene chloride. The extracts were washed with water, dried, filtered and concentrated under reduced pressure to obtain 1.45 g of yellow oil which was dissolved in isopropyl ether. The insoluble substance was filtered and the residue was treated with active charcoal, filtered and concentrated to dryness under reduced pressure at 50° C. to obtain 1.24 g of the expected product.

STEP D: (E) 2-butenedioate of 3,4-dimethoxy N-methyl N-[5-(1-pyrrolidinyl)6,7,8,9-tetrahydro-5H-benzocyclohepten-6-yl]benzeneacetamide Using the procedure of Step C of Examples 5 and 6, 2.4 g of 3,4-dimethoxyphenyl acetic acid and 1.9 g of the product of Step C were reacted to obtain 2.7 g of product in the form of a base. Then, 1.9 g of the product were obtained in the form of a salt with 0.74 g of fumaric acid after two crystallizations from ethanol for 1.44 g of the expected salt melting at 158° C.

Analysis: Calculated: %C, 65.73, %H 7.58, %N 4.79; Found: 65.4, 7.2, 4.8.

EXAMPLE 15

(E) 2-butenedioate of (±) trans 3,4-dichloro-N-methyl-N-[5-(1-pyrrolidinyl)-6,7,8,9-tetrahydro-5H-benzocyclohepten-6-yl]-benzene acetamide Using the procedure of Example 14, 2 g of 3,4-dichlorophenyl acetic acid and 1.5 g of the product of Step C of Example 14 were reacted to obtain 3.27 of product in the form of a base. Then, 2,9 g of salt with 0.72 g of fumaric acid, which was crystallized twice from ethanol yielded 2.6 g of the expected salt melting at 292° C.

Analysis: Calculated: %C 61.43, %H 5.89, %Cl 12.95, %N 5.12; Found: 61.2, 5.9, 13.0, 5.0.

EXAMPLE 16

Hydrochloride of trans (±) 2-(3,4-dichlorophenoxy)-N-methyl-N-[6-(1-pyrrolidinyl)-6,7,8,9-tetrahydro-5H-benzocyclohepten-5-yl]-acetamide Using the procedure of Step C of Examples 5 and 6, 620 mg of 3,4-dichlorophenoxy acetic acid and 492 mg of the product of Step B of Examples 5 and 6 were reacted to obtain 1.1 g of the crude product which was crystallized from ethyl ether to obtain 432 mg of product in the form of its hydrochloride. It was crystallized first from ethyl acetate and methanol and secondly from isopropanol and methanol to obtain 243 mg of the expected product in the form of its hydrochloride melting at 190° C.

Analysis: Calculated: %C 59.58, %H 6.04, %Cl 21.98, %N 5.79; Found: 59.7, 6.0, 21.9, 5.7.

EXAMPLE 17

Trans (±) 2-(3,4-dichlorophenoxy)-N-methoxy-N-[2-(1-pyrrolidinyl)-1,2,3,4-tetrahydro-1-naphthyl]-acetamide and its hydrochloride Using the procedure of Step C of Example 1, 1.4 g of 3,4-dichlorophenoxy acetic acid and 1.2 g of the product of Step B of Example 1 were reacted to obtain 2.8 g of crude product which was purified by chromatograph on silica (eluant: methylene chloride 95 methanol 0.5) to obtain 1.4 g of the expected product in the form of a base.

The product was converted to its hydrochloride by the addition of a hydrochloric acid/ ethyl acetate solution. After separation, 1.1 g of the product in the form of its hydrochloride was crystallized from methanol /ethyl ether to obtain 850 mg of hydrochloride melting at 185° C.

Analysis: Calculated: %C 58.8, %H 5.79, %N 5.96, %Cl 22.04; Found: 58.8, 5.9, 5.8. 22.4.

EXAMPLES 18 AND 19

Hydrochloric of (1-α, 2-β) (±) 3,4-dichloro-N-α-dimethyl-N-[2-(1-pyrrolidinyl)-1,2,3,4-tetrahydro-1-naphthyl]-benzene acetamide Example 18: Diastereo isomer A
Example 19: Diastereo isomer B 1.7 g of 3,4-dichloro-α-methyl-benzene-acetic acid and 1.3 g of 1,1'-carbonylidiimidazole in 17 ml of tetrahydrofuran were stirred for 30 minutes at ambient temperature. 1 of the product of Step B of Example 1 was added, and the mixture was stirred for 6 hours at reflux. The tetrahydrofuran was eliminated under reduced pressure and 50 ml of a saturated sodium bicarbonate solution in 30 ml of water were added. After extraction with methylene chloride, the extracts were washed with a saturated solution of sodium chloride, dried and concentrated under reduced pressure. The crude product obtained was purified by chromatography on silica (eluant : methylene chloride 95 methanol 5) to obtain 1 g of the product corresponding to diastereo isomer A in the form of a base (Example 18) and 1 g of diastereo isomer B (Example 19) in the form of a base.

Obtaining the hydrochlorides 1 g of diastereo isomer A was dissolved in 8 ml of acidified isopropanol and acidified with hydrochloric acid in ethyl acetate and after concentrating, crystallization was started. 10 ml of ethyl acetate were added and the crystals were separated to obtain 560 mg of the product in the form of its hydrochloride which was crystallized from ethyl acetate to obtain 450 mg of the expected product melting at 200° C.

Analysis: Calculated: %C 61.61, %H 6.25, %N 5.99, %Cl 22.73; Found: 61.8, 6.4, 5.8, 22.8.

Hydrochloride of diastereo isomer B

Using the above procedure, 630 mg of the product were obtained in the form of hydrochloride which was crystallized from isopropanol to obtain 450 mg of the expected product melting at 255° C.

Analysis: Calculated: %C 61.61, %H 6.25, %N 5.99, %Cl 22.73; Found: 61.96, 6.5, 5.9, 22.9.

EXAMPLE 20

Trans (±) N-methyl-N-[2-(1-pyrrolidinyl)-1,2,3,4-tetrahydro-1-naphthyl]-4-benzo-[b]-thiophene acetamide Using the procedure of Step C of Example 1, 700 mg of 4-thionaphthene acetic acid and 700 mg of the product of Step 5 Example 1 were reacted to obtain 1.8 g of crude product which was purified by chromatography on silica (eluant : methylene chloride 9 methanol 1) to obtain 1.2 g of the product corresponding to the fraction having an Rf of 0.45. 400 mg of this product were taken up several times in 8 ml of ethyl ether and evaporated to dryness each time, under reduced pressure to obtain 350 mg of powdery colorless foam.

Analysis: Calculated: %C 74.22, %H 6.98, %N 6.93, %S 7.91; Found: 74.3, 7.2, 6.5, 7.5.

EXAMPLE 21

Trans (±) 3,4-dichloro-N-[7-nitro-2-(1-pyrrolidinyl)-1,2,3,4-tetrahydro-1-naphthyl]-N-methyl-benzene acetamide

STEP A: Trans (±) 7-nitro-1-(1-pyrrolidinyl)-1,2,3,4-tetrahydro-2-naphthol

A mixture of 4.5 g of 7-nitro-1$a$,2,3,7$b$-tetrahydronaphtho [1,2-b] oxirene and 13.5 ml of water was stirred at 20 C. then cooled to 10° C. and over 15 minutes, 22.5 ml of a pyrrolidine were added. The mixture was stirred at 20 C. for 4 hours and 80 ml of water were added. The mixture was extracted with methylene chloride and the organic phase was washed with water, dried and the solvent is evaporated. 7 g of the expected product were obtained which were chromatographed on silica and eluted with an ethyl acetate—cyclohexane—triethylamine mixture (60-40-3) to obtain 5.43 g of the expected product as well as 0.7 g of the corresponding cis isomer. 5.43 g of the trans product were crystalized from an ethyl ether—petroleum ether mixture to obtain 4.30 g of the expected product melting at 77° C. After crystallization from the above mixture, a product which dissolved at 80° C. was obtained.

Analysis: Calculated: %C 64.11, %H 6.92, %N 10.678; Found: 64.3, 6.9, 10.7.

STEP B: Trans (±) 7-nitro-N-methyl-2-(1-pyrrolidinyl)-1,2,3,4-tetrahydro-1-naphthalene amine Using the procedure of Step B of Example 1, 1.31 g of the product of Step A, 10 ml of tetrahydrofuran, 0.90 m of triethylamine and 0.52 ml of methanesulfonyl chloride in 1.3 ml of tetrahydrofuran which is added at −20° C. were reacted. 7 ml of methylamine in solution at 33% in ethanol were used and after 1 hour of stirring, the solvent was evaporated. 50 ml of water saturated with sodium chloride and 2 ml of sodium hydroxide at 33% were added and extraction was done with methylene chloride. The organic phase was washed with water, dried and the solvent was evaporated to obtain 1.55 g of the expected product which was crystallized from isopropanol to obtain 1.03 g of product melting at 85° C.

Analysis: $C_{15}H_{21}N_2O_2$: molecular weight = 275.35 Calculated: %C 65.43, %H 7.69 %N 15.26; Found: 65.5, 7.8, 15.3.

STEP C: Trans (±) 3,4-dichloro-N-[7-nitro-2-(1-pyrrolidinyl)-1,2,3,4-tetrahydro-1-naphthyl]-N-methyl-benzene acetamide Using the procedure of Step C of Example 1, 1.82 g of 3,4-dichlorophenyl acetic acid and 1.5 g of the product of Step B were reacted to obtain 3 g of the expected product which was crystallized from ethyl ether to obtain 2.82 g of crystals melting at 133° C. The crystals were dissolved in a mixture of 10 ml of methylene chloride and 50 ml of isopropanol and a solution of hydrochloride acid in ethanol was added to a pH ≃ 2. The solution was concentrated and the crystals were separated to obtain 2.26 g of the expected product melting at 240° C. The product was crystallized from isopropanol.

Analysis: $C_{23}H_{25}Cl_2N_3O_3$ HCl : molecular weight 498.84, Calculated: %C 55.38, %H 5.25, %Cl 21.32, %N 8.42; Found: 55.6, 5.2, 21.3, 8.3.

Preparation of 7-nitro-1$a$,2,3,7$b$-tetrahydronaphth-[1,2,-b]-oxirene

1) 1,2-dihydro-7-nitro-naphthalene.

4 g of 7-nitro-1,2,3,4-tetrahydro-1-naphthalenol [J. Pharm. Soc., Jan, Vol. 64, (1944), p. 153], 53 ml of toluene and 180 mg of p-toluene sulfonic acid were mixed together and then stirred for 2 hours at 130° C. while distilling off ≃ 20 ml of solvent. Then, at 20° C. 50 ml of water were added and extraction was done with ethyl acetate. The extracts were washed with a saturated aqueous solution of sodium bicarbonate, and with a saturated aqueous solution of sodium chloride, dried and concentrated to dryness. The residue was crystalized from ethanol to obtain 2.75 g of the expected product melting at ≃35° C. and after crystallizing from isopropanol melting at 37° C.

Analysis: $C_{10}H_9NO_2$: molecular weight = 175.19, Calculated: %C 68,56, %H 5.18, %N 8.00; Found: 68.4, 5.1, 7.8.

2) 7-nitro-1$a$,2,3,7$b$-tetrahydro-naphth-[1,2-b]-oxirene 2.45 g of the product of Step 1, 36 ml of methylene chloride, 47 ml of 0.5N sodium bicarbonate solution and 3.40 g of metachloroperbenzoic acid were stirred at 20 C. for 5 hours. 0.7 g of per-acid and 9.30 ml of bicarbonate solution were added after 2 hours. After decanting, extraction was done with methylene chloride and the extracts were washed with water, dried and the solvent was evaporated. After crystallization from ether, 1.6 g of the expected product melting at 67° C. and after crystallization from isopropanol melting at 73° C. were obtained.

Analysis: %$C_{10}H_9HO_3$: molecular weight = 191.19 Calculated: %C 62.82, %H 4.75, %N 7.33; Found: 62.6, 4.7, 7.2.

EXAMPLE 22

Tablets were prepared containing 200 mg of the product of Example 20 and sufficient excipient of lactose, talc, starch and magnesium stearate for a final weight of 800 mg.

EXAMPLE 23

An injectable solution (intra-muscular route) was prepared containing 50 mg of the product of Example 2 and sufficient sterile solvent for a final volume of 5 ml

PHARMACOLOGICAL DATA

1) Binding of the opiate receptor K in vitro

Membranous sediment preserved at −30° C. (possibly for 30 days) and prepared from guinea pig cerbelli were used. The sediments were put in suspension in the buffer Tris pH 7.7. Fractions of 2 ml were distributed in hemolysis tubes and $^3$H ethylketocyclazocine 1 nM and the product to be studied were added. The following were determined: the mixture quantity of fixed radioactivity in the presence of $^3$H ethylketocyclazocine alone, the quantity of radioactivity bonded in a non-specific manner in the presence of the tritiated ligand and of an excess ($10^{-5}$ m) of the reference product known under the name of U-50488 H and the displacement of specific bonding produced by a dose of $5 \times 10^{-5}$M of the product to be tested.

These tests were carried out in triplicate and aliquotes of 2 ml were incubated at 25° C. for 40 minutes. After returning to 0° C. for 5 minutes at the end of the incubation, they were filtered with Whatman GF/C filters, rinsed in Tris buffer pH 7.7 and the radioactivity was counted in the presence of scintillating Triton. When the product to be tested displaced the specifically fixed radioactivity by more than 50%, the 50% inhibiting concentration ($CI_{50}$) was determined by a 7 dose scale. The results of the 50% inhibiting concentration were then expressed in nM. The $CI_{50}$ was therefore the concentration of the product studied, expressed in nM, necessary to displace 50% of the specifically fixed radioactivity on the receptor studied (LAHTI et al., 1982, Life Sci., Vol. 31, 2257) The results are as follows:

| Product of Example | $CI_{50}$ in nM |
| --- | --- |
| 2 | 12 |
| 3 | 11 |
| 20 | 3.3 |

Evaluation of diuretic activity

Male Sprague Dawley rats of 180–200 g weight were left without food for 17 hours before the experiment while receiving water ad libitum. Groups of 8 animals were made up per dose tested and the rats received the product to be tested or its vehicle sub-cutaneously. The volume of urine was measured each hour for the 2 hours following the administration of the product. At the end of this period, the urine was collected and the activity of the product was expressed as the percentage variation calculated on the urinary volume corresponding to the period $t_{1h}$–$t_{2h}$. The products of the invention showed a notable activity in this test.

Various modifications of the products and methods of the invention may be made without departing from the spirit or scope thereof and it is to be understood that the invention is intended to be limited only as defined in the appended claims.

What we claim is:

1. A compound selected from the group consisting of all possible enantiomeric and diasteroisomeric forms of compounds of the formula

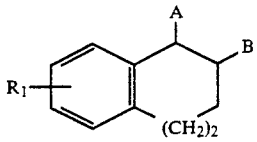

wherein $R_1$ is selected from the group consisting of hydrogen, halogen, alkyl and alkoxy of 1 to 5 carbon atoms, —$NO_2$, —$NH_2$ and mono and dialkylamino of 1 to 5 alkyl carbon atoms, A and B have the trans configuration, one of A and B being

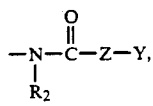

$R_2$ is hydrogen or alkyl of 1 to 5 carbon atoms, Z is —$(CH_2)_{n2}$, $n_2$ being an integer from 0 to 5 or branched alkylene of 2 to 8 carbon atoms or —$CH_2$—O—, Y is selected from the group consisting of phenyl, naphthyl, indenyl, and pyrrolidine all optionally having at least one substituent and the other of A and B is

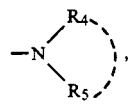

$R_4$ and $R_5$ individually being selected from the group consisting of hydrogen and alkyl of 1 to 5 carbon atoms or taken together with the nitrogen to which they are attached form pyrrolidine [a 5 to 6 ring heterocycle optionally containing a heteroatom selected from the group consisting of —O—, —S— and —NH—] and their non-toxic, pharmaceutically acceptable acid addition salts.

2. A compound of claim 1 wherein Y is selected from the group consisting of naphthyl, phenyl or phenyl substituted with at least one member of the group consisting of methyl, ethyl, ethoxy, methoxy, chlorine, bromine, —$CF_3$ and —$NO_2$.

3. A compound of claim 1 wherein $R_1$ is hydrogen, A is

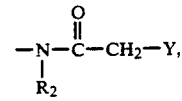

Y is selected from the group consisting of 3,4-dimethoxy-phenyl, 3,4-dichloro-phenyl, 4-trifluoromethyl-phenyl and 4-nitro-phenyl and B is pyrrolidinyl.

4. Compound of claim 1 selected from the group consisting of (5α,6β) (±) 3,4-dichloro-N,α-dimethyl-N-[6-(1-pyrrolidinyl)-6,7,8,9-tetrahydro-5H-benzocyclohepten-5-yl] benzene-acetamide and its non-toxic, pharmaceutically acceptable acid addition salts.

5. A compound of claim 1 selected from the group consisting of (E) butendioate of (±) (trans) 3,4-dimethoxy-N-methyl-N-[6-(1-pyrrolidinyl)-6,7,8,9-tetrahydro-5H-benzocyclohepten-5-yl]-benzene acetamide and its non-toxic, pharmaceutically acceptable acid addition salts.

6. A compound of claim 1 selected from the group consisting of trans (+) N-methyl-N-[6-(1-pyrrolidinyl)-6,7,8,9-tetrahydro-5H-benzocyclohepten-5-yl]-1-naphthalene-acetamide and its non-toxic, pharmaceutically acceptable acid addition salts.

7. An analgesic composition comprising an analgesically effective amount of a compound of claim 1 and an inert pharmaceutical carrier.

8. A composition of claim 7 wherein Y is selected from the group consisting of naphthyl, phenyl or phenyl substituted with at least one member of the group consisting of methyl, ethyl, ethoxy, methoxy, chlorine, bromine, —CF$_3$ and —NO$_3$.

9. A composition of claim 7 wherein R$_1$ is hydrogen, A is

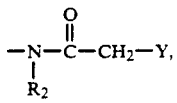

Y is selected from the group consisting of 3,4-dimethyl-phenyl, 3,4-dichloro-phenyl, 4-trifluoromethyl-phenyl and 4-nitro-phenyl and B is pyrrolidinyl.

10. A composition of claim 7 wherein the active compound is selected from the group consisting of (5α,6β) (±) 3,4-dichloro-N,α-dimethyl-N-[6-(1-pyrrolidinyl)-6,7,8,9-tetrahydro-5H-benzocyclohepten-5-]benzene acetamide and its non-toxic, pharmaceutically acceptable acid addition salts.

11. A composition of claim 7 wherein the active compound is selected from the group consisting of (E) butendioate of (±) (trans) 3,4-dimethoxy-N-methyl-N-[6-(1-pyrrolidinyl)-6,7,8,9-tetrahydro-5H-benzocyclohepten-5-yl]benzene acetamide and its non-toxic, pharmaceutically acceptable acid addition salts.

12. A composition of claim 7 wherein the active compound is selected from the group consisting of trans (±) N-methyl-N-[6-(1-pyrrolidinyl)-6,7,8,9-tetrahydro-5H-benzocyclohepten-5-yl]-1-naphthalene acetamide and its non-toxic, pharmaceutically acceptable acid addition salts.

13. A method of relieving pain in warm-blooded animals comprising administering to warm-blooded animals an analgesically effective amount of at least one compound of claim 1.

14. A method of claim 13 wherein Y is selected from the group consisting of naphthyl, phenyl or phenyl substituted with at least one member of the group consisting of methyl, ethyl, ethoxy, methoxy, chlorine, bromine, —CF$_3$ and —NO$_2$.

15. A method of claim 13 wherein R$_1$ is hydrogen, A is

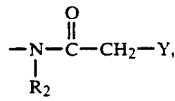

Y is selected from the group consisting of 3,4-dimethoxy-phenyl, 3,4-dichloro-phenyl, 4-trifluoromethyl-phenyl and 4-nitro-phenyl and B is pyrrolidinyl.

16. A method of claim 14 selected from the group consisting of (5α,6β) (±) 3,4-dichloro-N,α-dimethyl-N-[6-(1-pyrrolidinyl)-6,7,8,9-tetrahydro-5H-benzocyclohepten-5-yl benzene-acetamide and its non-toxic, pharmaceutically acceptable acid addition salts.

17. A method of claim 14 wherein the compound is selected from the group consisting of (E) butendioate of (trans) (±) 3,4-dimethoxy-N-methyl-N-[(6-(1-pyrrolidinyl)-6,7,8,9-tetrahydro-5H-benzoycyclohepten-5-yl]benzene acetamide and its on-toxic, pharmaceutically acceptable acid addition salts.

18. A method of claim 14 wherein the compound is selected from the group consisting of trans (±) N-methyl-N-[6-(1-pyrrolidinyl)-6,7,8,9-tetrahydro-5H-benzocyclohepten-5-yl]-1-naphthalene-acetamide and its non-toxic, pharmaceutically acceptable acid addition salts.

* * * * *